US010390951B2

(12) United States Patent
Creaven et al.

(10) Patent No.: US 10,390,951 B2
(45) Date of Patent: Aug. 27, 2019

(54) CLOCKING VALVE RETAINER

(71) Applicant: Medtronic Vascular Galway, Ballybrit, Galway (IE)

(72) Inventors: Marian Creaven, Ballybrit (IE); Niall Duffy, Ballybrit (IE)

(73) Assignee: MEDTRONIC VASCULAR GALWAY, Galway (IE)

( * ) Notice: Subject to any disclaimer, the term of this patent is extended or adjusted under 35 U.S.C. 154(b) by 155 days.

(21) Appl. No.: 15/446,352

(22) Filed: Mar. 1, 2017

(65) Prior Publication Data
US 2017/0172740 A1   Jun. 22, 2017

Related U.S. Application Data

(62) Division of application No. 13/944,284, filed on Jul. 17, 2013, now Pat. No. 9,615,923.

(51) Int. Cl.
*A61F 2/24*   (2006.01)

(52) U.S. Cl.
CPC .......... *A61F 2/2436* (2013.01); *A61F 2/2412* (2013.01); *A61F 2220/0016* (2013.01); *A61F 2250/0089* (2013.01); *A61F 2250/0097* (2013.01); *Y10T 29/49902* (2015.01)

(58) Field of Classification Search
CPC ........ A61F 2/2436; A61F 2/2418; A61F 2/95; A61F 2/2427; A61F 2/966; A61F 2/2412; A61F 2/91; A61F 2/962; A61F 2002/9517; A61F 2002/9665; A61F 2002/9522; A61F 2002/9505; A61M 2205/583; A61M 2005/3126; A61M 2005/2403; A61M 2205/581; A61M 5/31551; A61B 17/0401; A61B 17/861; A61B 17/8897; A61B 17/00; A61B 17/00234; A61B 17/0057; A61B 2017/00243; A61B 2017/0409; A61B 2017/0458; A61B 2017/1205
See application file for complete search history.

(56) References Cited

U.S. PATENT DOCUMENTS

| | | |
|---|---|---|
| 3,787,982 A | 1/1974 | Anderson |
| 5,733,325 A | 3/1998 | Robinson et al. |
| 6,267,783 B1 | 7/2001 | Letendre et al. |
| 6,673,106 B2 | 1/2004 | Mitelberg et al. |
| 8,052,732 B2 | 11/2011 | Mitchell et al. |
| 8,398,708 B2 | 3/2013 | Meiri et al. |
| 2009/0287290 A1 | 11/2009 | Macaulay et al. |
| 2010/0049313 A1 | 2/2010 | Alon et al. |
| 2010/0100167 A1 | 4/2010 | Bortlein et al. |
| 2011/0098805 A1 | 4/2011 | Dwork et al. |
| 2011/0251675 A1 | 10/2011 | Dwork |

(Continued)

*Primary Examiner* — David C Eastwood
*Assistant Examiner* — Mohamed G Gabr
(74) *Attorney, Agent, or Firm* — Medler Ferro Woodhouse & Mills PLLC

(57) ABSTRACT

Valve retainers and delivery systems with valve retainers are disclosed. In certain embodiments, a portion of the valve retainer can rotate about a central axis of the delivery system relative to a different portion of the valve retainer. In certain embodiments, a first portion of the valve retainer can include a plurality of first orientation markings. In certain embodiments, a second portion of the valve retainer can include a second orientation marking, which can be aligned with a first orientation marking on the first portion of the valve retainer.

8 Claims, 3 Drawing Sheets

(56) References Cited

U.S. PATENT DOCUMENTS

2011/0264203 A1  10/2011  Dwork et al.
2011/0295216 A1* 12/2011  Miller .................. A61F 2/2436
                                    604/264
2012/0158129 A1*  6/2012  Duffy .................... A61F 2/2427
                                    623/2.11

* cited by examiner

CLOCKING VALVE RETAINER

RELATED APPLICATIONS

This application is a Division of and claims the benefit of U.S. patent application Ser. No. 13/944,284 filed Jul. 17, 2013, now allowed. The disclosures of which are herein incorporated by reference in their entirety.

BACKGROUND

Field

The present disclosure relates to heart valve delivery systems and methods for loading prosthetic heart valves onto a delivery system. More specifically, the present disclosure relates to delivery systems having a rotatable valve retainer.

Background

Diseased or otherwise deficient heart valves can be repaired or replaced using heart valve surgery. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Minimally invasive approaches have been developed to facilitate catheter-based implantation of valve prostheses on the beating heart, intending to obviate the need for the use of classical sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a lumen within the body, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

With regard to the structure of the heart valve prosthesis itself, U.S. Pat. No. 7,914,569 to Nguyen et al. describes an example prosthesis for percutaneous transluminal delivery. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

Other techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter can be transcatheterally advanced toward the native valve, where it can be either forcefully deployed using a balloon catheter, or, alternatively, passively deployed using a self-expandable system.

In order to prepare such valve prostheses for implantation, the valve prosthesis can be initially provided in an expanded or uncrimped condition, then crimped or compressed around the catheter until it is as close to the diameter of the catheter as possible. Various methods and devices are available for crimping the valve onto the catheter, which may include hand-held devices or tabletop devices, for example.

Various attachment devices can be used for securing the crimped valve prosthesis onto the catheter. Current attachment devices, however, are generally limited in their configuration and do not provide the ability to customize the attachment location and/or orientation of the valve prosthesis based on the anatomical features of the patient's heart. For example, anatomical analysis of the mitral valve anatomy has shown variation in the position of the A2-P2 scallops from patient to patient. This variation can make it difficult to properly position and load onto a delivery system a prosthetic valve having an asymmetrical cross-section, for example, a prosthetic valve having support arms.

BRIEF SUMMARY

The present disclosure relates to heart valve delivery systems and methods for loading prosthetic heart valves onto a delivery system. More specifically, the present disclosure relates to delivery systems having a rotatable valve retainer. The delivery systems disclosed herein can be used for repairing or replacing any heart valve (e.g., mitral valve or aortic valve). Further, while the present disclosure is generally directed to delivery systems for heart valve prostheses, it is understood that the delivery systems and components thereof (e.g., embodiments of the valve retainers described herein) can be used with, or incorporated into, delivery systems for other medical devices.

In certain embodiments, the delivery system can include a valve retainer having a first portion and a second portion. In certain embodiments, the first portion can be a proximal portion and the second portion can be a distal portion. In certain embodiments, the first portion can be a distal portion and the second portion can be a proximal portion. In certain embodiments, the second portion of the valve retainer can include a groove. In certain embodiments, the delivery system can include an inner shaft and an outer sheath.

In certain embodiments, the second portion of the valve retainer can rotate about a central axis of the delivery system relative to the first portion of the valve retainer. In certain embodiments, the first portion of the valve retainer can include a plurality of first orientation markings. In certain embodiments, the second portion of the valve retainer can include a second orientation marking. In certain embodiments, the second portion can include one or more attachment locations.

In certain embodiments, the first orientation markings and the second orientation marking can be lines, for example, lines parallel to the central axis of the delivery system. In certain embodiments, the first and second orientation markings can be etched into an exterior surface of the first and second portions of the valve retainer, respectively. In certain embodiments, the first orientation markings can include a numerical value. In certain embodiments, the first portion of the valve retainer can have nine orientation markings. In certain embodiments, the second orientation marking can be aligned with one of the plurality of attachment locations on the second portion of the valve retainer.

In certain embodiments, the delivery system can include a valve support. In certain embodiments, the valve support can be located adjacent to the second portion of the valve retainer. In certain embodiments, the valve support can be located proximally from the second portion of the valve retainer. In certain embodiments, the valve support can have a first end with a first diameter and a second end with a second diameter, wherein the second diameter is smaller than the first diameter. In certain embodiments, the valve support can be connected to the second portion of the valve retainer. In certain embodiments, the valve support can be rotated about the central axis of the delivery system to lock the second portion and first portion of the valve retainer together.

Various embodiments of valve retainers are contemplated. In certain embodiments, a first portion of the valve retainer can include a plurality of first orientation markings and a second portion of the valve retainer can include a second orientation marking and a plurality of attachment locations. In certain embodiments, the second portion of the valve retainer can rotate about a central axis of the valve retainer relative to the first portion of the valve retainer.

In certain embodiments, the valve retainer can have a first end and a second end having a plurality of attachment locations. In certain embodiments, each attachment location can be identified by an orientation marking on an exterior surface of the valve retainer. In certain embodiments, the valve retainer can have nine attachment locations. In certain embodiments, the attachment locations can be equally spaced around the valve retainer. In certain embodiments, the orientation marking for each attachment location can be a numerical value.

Methods of loading a prosthetic valve onto a delivery system are also contemplated. In certain embodiments, a second portion of a valve retainer can be rotated to align a second orientation marking on the second portion of the valve retainer with one of a plurality of first orientation markings on a first portion of the valve retainer.

In certain embodiments, a prosthetic valve can be attached to the second portion of the valve retainer. In certain embodiments, one or more attachment members on the prosthetic valve can be attached at one or more attachment locations on the second portion of the valve retainer. In certain embodiments, the attachment location can be aligned with the second orientation marking on the second portion of the valve retainer. In certain embodiments, multiple attachment members on the prosthetic valve can be attached at multiple attachment locations on the second portion of the valve retainer. In certain embodiments, the valve retainer can have a number of attachment locations corresponding to a multiple of the number of attachment members on the prosthetic valve. In certain embodiments, a prosthetic valve has three attachment members and a valve retainer has nine attachment locations. In certain embodiments, a prosthetic valve has two attachment members and a valve retainer has eight attachment locations.

In certain embodiments, a valve support attached to the second portion of the valve retainer can be rotated to lock the second portion and first portion of the valve retainer together.

In certain embodiments, medical imaging of a heart can be used to determine which of the first orientation markings on the first portion of the valve retainer with which to align the second orientation marking on the second portion of the valve retainer.

BRIEF DESCRIPTION OF THE DRAWINGS/FIGURES

The accompanying figures, which are incorporate herein, form part of the specification and illustrate embodiments of valve retainers. Together with the description, the figures further to serve to explain the principals of and allow for the making and using of the delivery systems and valve retainers described herein. These figures are intended to be illustrative, not limiting. Although the disclosure is generally described in the context of these embodiments, it should be understood that it is not intended to limit the scope of the disclosure to these particular embodiments. In the drawings, like reference number indicate identical or functionally similar elements.

DETAILED DESCRIPTION

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting.

Further, it is understood that the devices and methods described herein can be implemented in many different embodiments of hardware. Any actual hardware described is not meant to be limiting. The operation and behavior of the device, systems, and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1:
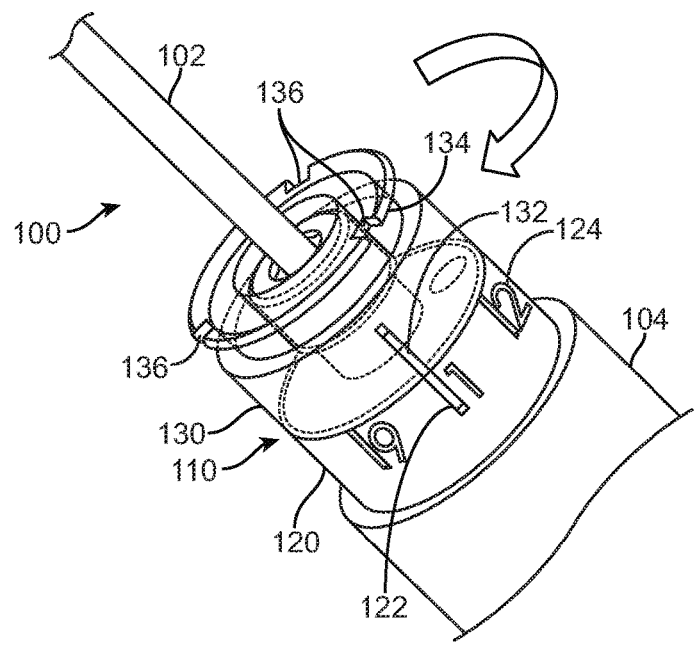
FIG. 1 illustrates a perspective view of a rotatable valve retainer for a delivery system, according to an embodiment.

FIG. 1 illustrates delivery system 100, according to an embodiment. In certain embodiments, delivery system 100 can include inner shaft 102, outer sheath 104, and valve retainer 110. In certain embodiments, valve retainer 110 can include first portion 120 and second portion 130. In certain embodiments, inner shaft 102 can comprise one or more lumens.

Inner shaft 102, outer sheath 104, and valve retainer 110 can be made from any suitable material, for example, but not limited to, plastic or metal. In certain embodiments, first portion 120 and second portion 130 of valve retainer 110 can be different materials. For example, in certain embodiments, first portion 120 can be metal and second portion 130 can be plastic.

Figure 4:
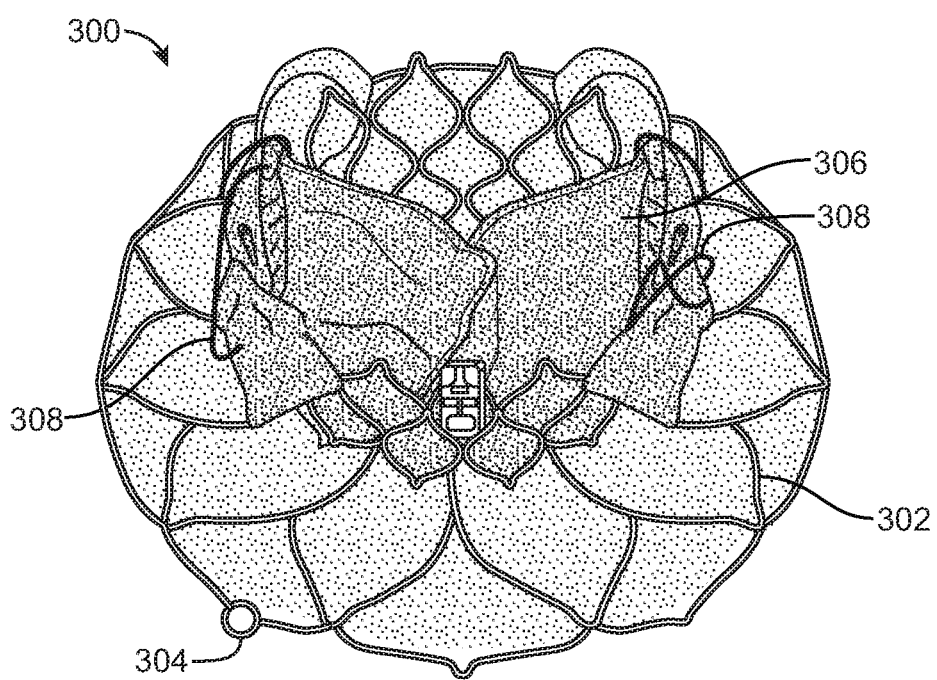
FIG. 4 illustrates a heart valve, according to an embodiment.

FIG. 4 illustrates prosthetic valve 300 according to an embodiment. In certain embodiments, prosthetic valve 300 can include frame 302, one or more attachment members 304, valve portion 306, and one or more support arms 308. In certain embodiments, attachment member 304 can be configured to attach prosthetic valve 300 to a valve retainer. In certain embodiments, attachment member 304 can be an eyelet. In certain embodiments, attachment member 304 can be, for example, a hook, barb, loop, wire, protrusion, or any other suitable mechanism for attaching prosthetic valve 300 to second portion 130 of valve retainer 110. In certain embodiments, one or more attachment members 304 may be unique relative to the other attachment members. In certain embodiments, a unique attachment member 304 can be a different shape, color, material, etc., making it easily identifiable and easy to distinguish from other attachment members. This unique attachment member 304 can be used as an indicator for determining the orientation position of prosthetic valve 300 when loaded onto valve retainer 110.

In certain embodiments, as shown, for example, by the arrow in FIG. 1, second portion 130 of valve retainer 110 can rotate about an axis of delivery system 100. In certain embodiments, first portion 120 can be stationary, such that second portion 130 rotates relative to first portion 120. In certain embodiments, second portion 130 can rotate in both the clockwise and counterclockwise directions. In certain embodiments, second portion 130 can only rotate in a clockwise direction. In other embodiments, second portion 130 can only rotate in a counterclockwise direction. Allowing second portion 130 to rotate can control the delivery and deployment orientation of support arms 308 of prosthetic valve 300 (see FIG. 4.)

In certain embodiments, first portion 120 of valve retainer 110 can include one or more first orientation markings 122. In certain embodiments, first orientation markings 122 can be a line. Other markings can be used for first orientation markings 122, for example, but not limited to, dashes, crosses, shapes, etc. In certain embodiments, first orientation markings 122 can be incorporated onto an exterior surface of first portion 120 (e.g., by printing, painting, screening, etc.). In certain embodiments, first orientation markings 122 can be etched into first portion 120, forming an indentation in the exterior surface of first portion 120. In certain embodiments, first orientation markings 122 can be raised to protrude from the exterior surface of first portion 120.

In certain embodiments, first portion 120 can include indicators 124. In certain embodiments, indicators 124 can be numbers. Indicators 124 are not limited to numbers, and can be, for example, letters, shapes, symbols, etc. Indicators 124 can be incorporated onto first portion 120 in any of the manners described above with respect to first orientation markings 122.

In certain embodiments, second portion 130 of valve retainer 110 can include one or more second orientation marking 132. Second orientation marking 132 can take any of the forms described above with respect to first orientation marking 122. By way of non-limiting example, in certain embodiments, second orientation marking 132 can be a line etched into an exterior surface of second portion 130. Second orientation marking 132 can be larger, smaller, or equal in size (e.g., length and width) as compared to first orientation marking 122. As shown in FIG. 1, second orientation marking 132 can be aligned with one of the first orientation markings 122. However, in other embodiments, orientation markings 122 and 132 can be offset.

Generally, second portion 130 can be rotated to align second orientation marking 132 with one of the first orientation markings 122 on first portion 120. In certain embodiments, this can facilitate orienting prosthetic valve 300 is a desired position so that upon delivery, support arms 308 properly align with the native valve. In certain embodiments, second portion 130 can rotate smoothly about an axis of delivery system 300, such that second orientation marking 132 can align with one of the first orientation markings 122 or be between two the first orientation markings 122. In certain embodiments, second portion 130 can be biased to align second orientation marking 132 with one of the first orientation markings 122, such that second orientation marking 132 tends to be aligned with one of the first orientation markings 122. For example, second portion 130 can click or lock into place when second orientation marking 132 is aligned with one of the first orientation markings 122.

In certain embodiments, second portion 130 can include groove 134. Groove 134 can be configured to receive and hold in place one or more attachment members 304 of prosthetic valve 300.

In certain embodiments, second portion 130 can include one or more attachment locations 136. Attachment locations 136 can facilitate attaching prosthetic valve 300 to second portion 130 of valve retainer 110. In certain embodiments, the number of attachment locations 136 can be greater than the number of attachment members 304 on prosthetic valve 300. In certain embodiments, the number of attachment locations 136 can be a multiple of the number of attachment members 304 on prosthetic valve 300.

Attachment locations 136 can be, for example, slots, hooks, barbs, clips, indentations, protrusions, or any other suitable mechanism for attaching prosthetic valve 300 to second portion 130 of valve retainer 110. In certain embodiments, attachment locations 136 can be configured to mate with attachment members 304 of prosthetic valve 300. In certain embodiments, attachment locations 136 can be pre-configured at specification locations on second portion 130 of valve retainer 110. In certain embodiments, one attachment location 136 can be aligned with second orientation marking 132. In certain embodiments, a unique attachment member 304 on prosthetic valve 300 can be attached at the attachment location 136 aligned with second orientation marking 132. This can quickly and easily indicate the orientation of prosthetic valve 300. In certain embodiments, medical imaging can be used to determine which first orientation markings 122 to align second orientation marking 132 with so that prosthetic valve 300 can be delivered with the proper orientation to best fit the native valve.

Figure 2:
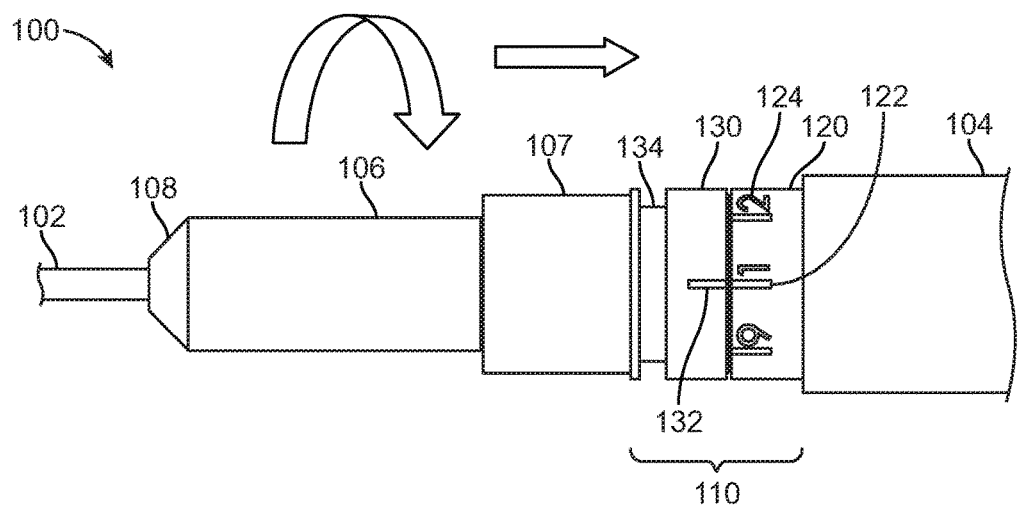
FIG. 2 illustrates a side view of a rotatable valve retainer for a delivery system, according to an embodiment.

FIG. 2 illustrates delivery system 100, according to an embodiment. In addition to the features illustrated in FIG. 1, the embodiment shown in FIG. 2 illustrates valve support 106. In certain embodiments, valve support 106 can have first end 107 and second end 108. In certain embodiments, first end 107 of valve support 106 can be larger in diameter than second end 108. In certain embodiments, second end 108 of valve support 106 can be tapered.

As shown by the arrow in FIG. 2, in certain embodiments, valve support 106 can be rotated about an axis of delivery system 100. In certain embodiments, rotating valve support 106 can move valve support 106 in a direction toward valve retainer 110, as indicated by the arrow in FIG. 2, thereby locking valve retainer 110 in place. In certain embodiments, valve support 106 can have a threaded interior and rotate about inner shaft 102, which can have a threaded exterior surface. In certain embodiments, the force (e.g., friction force or compression force) applied by valve support 106 can prevent second portion 130 of valve retainer 110 from rotating with respect to first portion 120.

Figure 3:
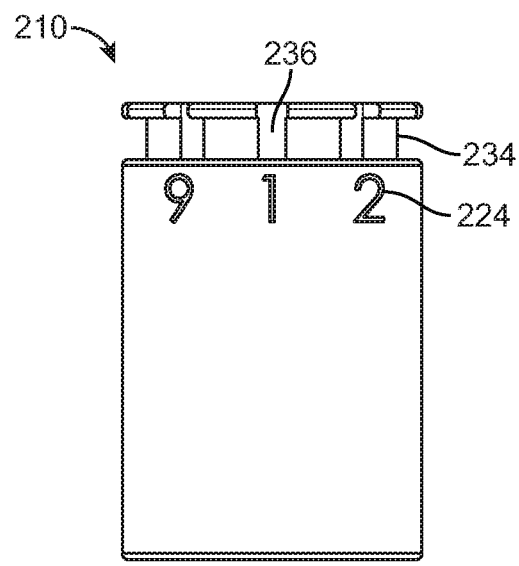
FIG. 3 illustrates a valve retainer, according to an embodiment.

FIG. 3 illustrates valve retainer 210, according to an embodiment. In certain embodiments, valve retainer 210 can include markings 224, groove 234, and more than one attachment locations 236. In comparison to the embodiment shown in FIG. 1, which can provide customized orientation of a loaded valve prosthesis by rotating a portion of the valve retainer, the embodiment illustrated in FIG. 3 can provide customized orientation because of the number of attachment locations 236 located on valve retainer 210.

In certain embodiments, attachment locations 236 can facilitate attaching prosthetic valve 300 to valve retainer 210. Attachment locations 236 can be, for example, slots, hooks, barbs, clips, indentations, protrusions, or any other suitable mechanism for attaching prosthetic valve 300 to valve retainer 210. In certain embodiments, attachment locations 236 can be configured to mate with attachment members 304 of prosthetic valve 300. In certain embodiments, the number of attachment locations 236 can be greater than the number of attachment members 304 on prosthetic valve 300. In certain embodiments, the number of attachment locations 236 can be a multiple of the number of attachment members 304 on prosthetic valve 300. In certain embodiments, valve retainer 210 can include nine attachment locations 236.

In certain embodiments, valve retainer 210 can include markings 224, which can be, for example, a line. In certain embodiments, markings 224 can include numbers. Other markings, for example, but not limited to, dashes, crosses, shapes, letters, symbols, etc. can be used for markings 224. In certain embodiments, markings 224 can be incorporated onto an exterior surface of valve retainer 210 (e.g., by printing, painting, screening, etc.). In certain embodiments, markings 224 can be etched into valve retainer 210, forming an indentation in the surface of valve retainer 210. In certain embodiments, markings 224 can be raised to protrude from the surface of valve retainer 210.

Figure 5A:
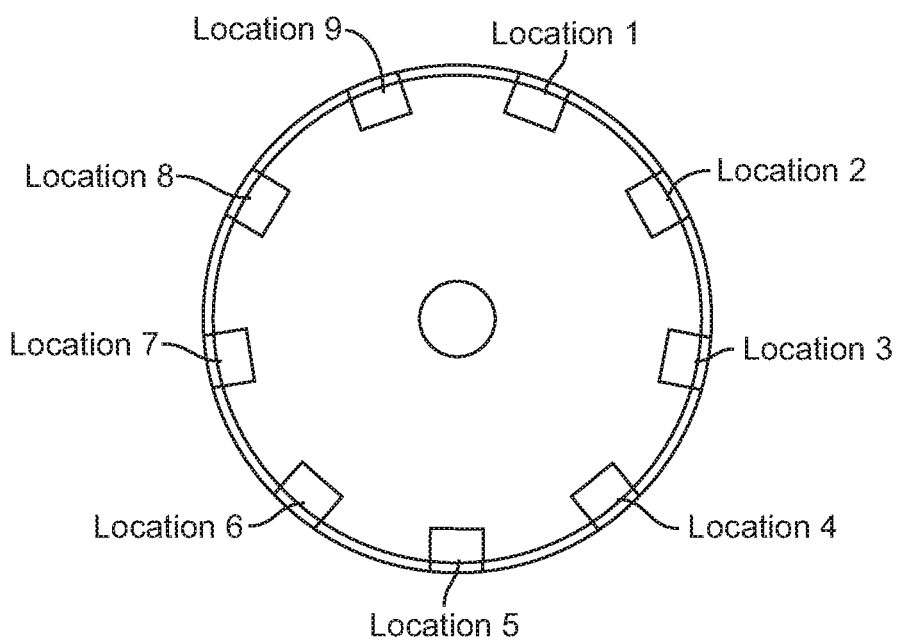
FIG. 5A illustrates attachment locations on a valve retainer, according to an embodiment.
Figure 5B:
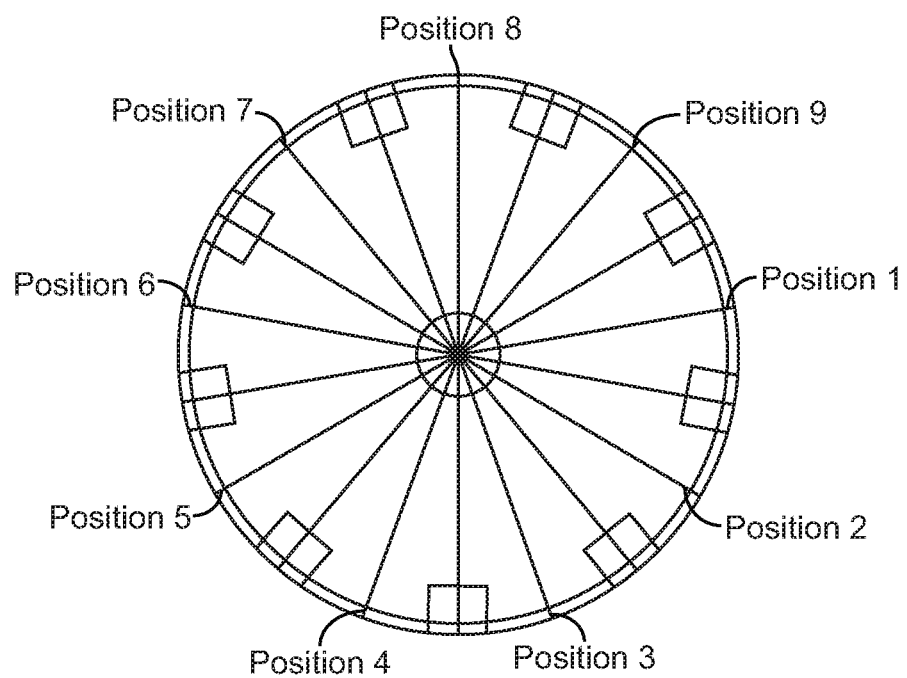
FIG. 5B illustrates positions of support arms about a valve retainer, according to an embodiment.

Embodiments of valve retainer 210, for example the embodiments illustrated in FIGS. 3 and 5A-5B, provide advantages over present valve retainers. Certain existing valve retainers include the same number of attachment locations as the number of attachment members on the prosthetic valve to be delivered. For example, certain existing valve retainers include only three attachment locations for attaching the attachment members of a prosthetic valve. This only allows for three positions of the support arms. Even assuming that the prosthetic valve has two support arms located opposite each other and that the delivery system can be rotated by 20 degrees (e.g., 10 degrees clockwise, 10 degrees counter-clockwise; or 5 degrees clockwise, 15 degrees counter-clockwise), the three attachment locations only provide only 120 degrees of positioning coverage around the valve retainer. This is only one-third of the possible area.

However, by providing nine attachment locations 236, valve retainers disclosed herein, for example, valve retainer 210 in FIG. 3, can provide a full 360 degrees of coverage for the location of the support arms. Under the same assumptions indicated above, that the prosthetic valve has two support arms located opposite each other and that the delivery system can be rotated by 20 degrees, valve retainer 210 can provide 360 degrees of positioning coverage.

By way of example, FIG. 5A illustrates a plurality of attachment locations on a valve retainer, according to an embodiment. In certain embodiments, the valve retainer can include nine such attachment locations. In certain embodiments, a unique attachment member 304 of prosthetic valve 300 can be attached at one of the nine attachment locations. In certain embodiments, medical imaging can be used to determine at which attachment location the unique attachment member 304 should be attached so that prosthetic valve 300 can be delivered with the proper orientation to best fit the native valve.

FIG. 5B illustrates a valve retainer having a plurality of support arm positions, according to an embodiment. In certain embodiments, the valve retainer can include nine such positions, as illustrated in FIG. 5B. By way of example, when the unique attachment member 304 is attached at Location 1 of FIG. 5A, a support arm 308 of prosthetic valve 300 can be located at Position 1, as indicated in FIG. 5B. In certain embodiments, a second support arm 308 of prosthetic valve 300 can be located opposite (e.g., 180 degrees from) Position 1. In this manner, when there are two support arms 308 and nine attachment locations, there are eighteen possible positions for the support arms 308. Assuming the delivery system can be rotated 20 degrees, an entire 360 degrees of coverage area can be provided.

Although illustrated using nine unique attachment locations, it is understood that the 360 degrees of positioning coverage can be achieved by having a greater or lesser number of attachment locations. For example, 6-12 evenly spaced attachment locations are contemplated, having 360 degrees of coverage area.

Methods of loading a prosthetic valve onto a delivery system are also disclosed. In certain embodiments, second portion 130 of valve retainer 110 can be rotated to align second orientation marking 132 on second portion 130 of valve retainer 110 with one of the plurality of first orientation markings 122 on first portion 120 of valve retainer 110.

In certain embodiments, prosthetic valve 300 can be attached to second portion 130 of the valve retainer 110, before or after rotating second portion 130 of valve retainer 110 to align second orientation marking 132 with one of the plurality of first orientation markings 122. For example, in certain embodiments, attachment member 304 of prosthetic valve 300 can be attached to attachment location 136 of second portion 130 of valve retainer 110. In certain embodiments, attachment location 136 can be aligned with second orientation marking 132.

In certain embodiments, valve support 106 can be rotated to lock valve retainer 110, such that second portion 130 cannot rotate with respect to first portion 120. In certain embodiments, medical imaging of a patient's heart can be used to determine which of the first orientation markings 122 with which to align second orientation marking 132.

The foregoing description has been presented for purposes of illustration and description. It is not intended to be exhaustive or to limit the precise embodiments disclosed. Other modifications and variations may be possible in light of the above teachings.

The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A method of loading a prosthetic valve onto a delivery system comprising:

rotating a second portion of a valve retainer to align a second orientation marking disposed on a radial outer surface of the second portion of the valve retainer with one of a plurality of first orientation markings disposed on a radial outer surface of a first portion of the valve retainer, wherein a proximal end of the second orientation marking on the outer surface of the second portion is distal to a distal end of the one of the plurality of first orientation markings on the outer surface of the first portion, and wherein the first portion and the second portion are axially fixed; and attaching the prosthetic valve to the second portion of the valve retainer, wherein attaching the prosthetic valve comprises attaching an attachment member on the prosthetic valve to an attachment structure on the second portion of the valve retainer, and wherein the attachment structure is distal of and longitudinally aligned with the second orientation marking on the second portion of the valve retainer.

2. The method of claim 1, further comprising rotating a valve support attached to the second portion of the valve retainer to lock the second portion and first portion of the valve retainer together.

3. The method of claim 1, further comprising using medical imaging of a heart to determine which of the first orientation markings on the first portion of the valve retainer with which to align the second orientation marking on the second portion of the valve retainer.

4. The method of claim 1, wherein the attachment structure on the second portion of the valve retainer is one of a number of attachment structures on the second portion of the valve retainer, and the attachment member on the prosthetic valve is one of a number of attachment members on the prosthetic valve, and wherein the number of attachment structures on the second portion of the valve retainer is greater than the number of attachment members on the prosthetic valve.

5. A method of loading a prosthetic valve onto a delivery system comprising:

rotating a second portion of a valve retainer about a central axis of the delivery system relative to a first portion of the valve retainer to align a second orientation marking on a radial outer surface of the second portion of the valve retainer with one of a plurality of first orientation markings on a radial outer surface of the first portion of the valve retainer, wherein the first portion of the valve retainer is disposed proximal of the second portion of the valve retainer such that a proximal end of the second orientation marking on the outer surface of the second portion is distal to a distal end of the one of the plurality of first orientation markings on the outer surface of the first portion, and wherein the first portion and the second portion are axially fixed; and attaching the prosthetic valve to the second portion of the valve retainer at an attachment structure of the second portion that is distal to the second orientation marking.

6. The method of claim 5, further comprising rotating a valve support attached to the second portion of the valve retainer to lock the second portion and the first portion of the valve retainer together.

7. The method of claim 5, wherein attaching the prosthetic valve comprises attaching an attachment member on the prosthetic valve at the attachment structure on the second portion of the valve retainer, and wherein the attachment structure is longitudinally aligned with the second orientation marking on the outer surface of the second portion of the valve retainer.

8. The method of claim 7, wherein the attachment structure on the second portion of the valve retainer is one of a number of attachment structures on the second portion of the valve retainer, and the attachment member on the prosthetic valve is one of a number of attachment members on the prosthetic valve, and wherein the number of attachment structures on the second portion of the valve retainer is greater than the number of attachment members on the prosthetic valve.

* * * * *